(12) United States Patent
Akahori

(10) Patent No.: US 7,095,882 B2
(45) Date of Patent: Aug. 22, 2006

(54) MEDICAL IMAGE PROCESSING METHOD AND MEDICAL IMAGE PROCESSING APPARATUS

(75) Inventor: Sadato Akahori, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 659 days.

(21) Appl. No.: 09/987,377

(22) Filed: Nov. 14, 2001

(65) Prior Publication Data
US 2002/0141630 A1 Oct. 3, 2002

(30) Foreign Application Priority Data
Nov. 22, 2000 (JP) .............................. 2000-355333

(51) Int. Cl.
G06K 9/00 (2006.01)
(52) U.S. Cl. ..................................... 382/132
(58) Field of Classification Search ................ 382/128, 382/131, 132; 378/98–98.12, 37, 165; 600/407, 600/415
See application file for complete search history.

(56) References Cited

U.S. PATENT DOCUMENTS

| 6,055,326 | A  | * | 4/2000  | Chang et al.   | 382/132  |
| 6,266,453 | B1 | * | 7/2001  | Hibbard et al. | 382/294  |
| 6,459,925 | B1 | * | 10/2002 | Nields et al.  | 600/427  |
| 6,504,897 | B1 | * | 1/2003  | Yonekawa       | 378/63   |
| 6,687,331 | B1 | * | 2/2004  | Muller et al.  | 378/98.5 |
| 2003/0228041 | A1 | * | 12/2003 | Bae et al. | 382/131 |

FOREIGN PATENT DOCUMENTS

| JP | 3-287248 | 12/1991 |
| JP | 8-294479 | 11/1996 |
| JP | 9-238933 | 9/1997 |

\* cited by examiner

*Primary Examiner*—Joseph Mancuso
*Assistant Examiner*—Ashutosh Upreti
(74) *Attorney, Agent, or Firm*—Sughrue Mion, PLLC

(57) ABSTRACT

A medical image processing apparatus can change an output image in accordance with photographing condition. The medical image processing apparatus for processing image data representing an image obtained by radiography and read by an image reading apparatus, comprises: a unit for receiving the image data and photographing condition when the image is obtained; a unit for executing image processing of the image data; and a unit for reading output-format control information corresponding to the photographing condition from a predetermined set of output-format control information to be used to control an image format when the image is output on a film.

15 Claims, 8 Drawing Sheets

PHOTOGRAPHS FROM LEFT-HAND AND RIGHT-HAND SLANTING UPSIDES

PHOTOGRAPHS FROM JUST ABOVE ON LEFT-HAND AND RIGHT-HAND SIDES

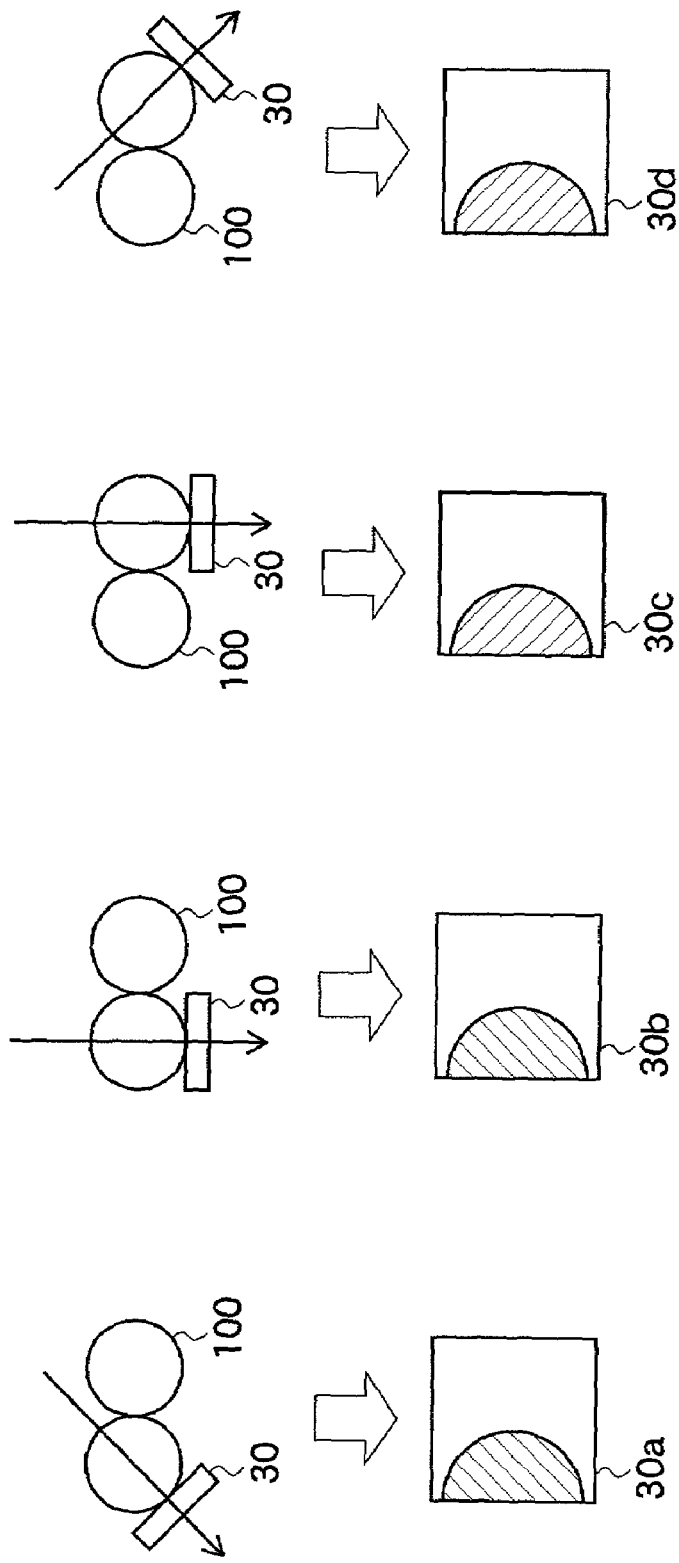

FIG.4

| PHOTOGRAPHING CONDITION | OUTPUT POSITION | ROTATION | POSITION ADJUSTMENT |
|---|---|---|---|
| (A) RIGHT-HAND BREAST, SLANTING UPSIDE | FIRST FRAME | 180 DEGREES ROTATION | RIGHTWARD MOVEMENT |
| (B) RIGHT-HAND BREAST, JUST ABOVE | THIRD FRAME | 180 DEGREES ROTATION | RIGHTWARD MOVEMENT |
| (C) LEFT-HAND BREAST, JUST ABOVE | FOURTH FRAME | NONE | LEFTWARD MOVEMENT |
| (D) LEFT-HAND BREAST, SLANTING UPSIDE | SECOND FRAME | NONE | LEFTWARD MOVEMENT |

← PHOTOGRAPHS FROM LEFT-HAND AND RIGHT-HAND SLANTING UPSIDES

← PHOTOGRAPHS FROM JUST ABOVE ON LEFT-HAND AND RIGHT-HAND SIDES

MEDICAL IMAGE PROCESSING METHOD AND MEDICAL IMAGE PROCESSING APPARATUS

BACKGROUND OF THE INVENTION

1. Field of the Invention

The present invention relates to medical image processing method and apparatus for processing a medical image photographed by using radiation, etc.

2. Description of a Related Art

Photography using radiation (X-ray, α-ray, β-ray, γ-ray, electron beam, ultraviolet ray and so on) is conventionally utilized in various fields, and is one of most important means for a diagnosis particularly in a medical field. An X-ray radiography is variously improved since the realization of a first X-ray radiograph, and a method using combination of a fluorescent screen and an X-ray film is a main current at present. In recent years, various digitalized devices such as an X-ray CT, an ultrasonic diagnosis and an MRI are practically used in a medical image diagnosis, and construction of diagnostic information processing systems, etc. within hospitals is going to be advanced. Many researches for the digitalization have been also made with respect to an X-ray image, and radiography using photostimulable phosphor is established and is practically used as a method to replace the conventional X-ray radiography.

Photostimulable phosphor (accumulative phosphor) is such substance that accumulates a part of radiation energy when irradiated with radiation and then generates photostimulated luminescence light in accordance with the accumulated energy when irradiated with excitation light such as a visible ray. Existence of the photostimulable phosphor was conventionally known. Radiography using the photostimulable phosphor is constructed as follows. That is, a radiation image of an object such as a human body is photographed and recorded on a sheet coated with the photostimulable phosphor. When the photostimulable phosphor sheet is scanned by excitation light such as a laser beam, photostimulated luminescence light is generated so that image data is obtained by photo-electrically reading the light. After the image data is suitably processed, an image represented by the image data is displayed on a display such as a CRT, or is printed on a film by a laser printer, etc. so that the radiation image can be displayed as a visible image.

Such radiography has performance equivalent to the conventional X-ray radiography in view of photographing sensitivity and image quality. For example, in comparison with the conventional X-ray radiography, an exposure area is very wide and a response of the photostimulated luminescence light to an exposure amount is approximately proportional to the exposure amount over the entire exposure area. Therefore, even when the object is photographed in any radiation amount, a luminescence area where the image exists can be grasped and normalized to be converted to a digital signal without under or over amounts. By combining the obtained signal with a suitable image processing method, an image of high quality can be steadily provided even under various kinds of photography condition. Further, since the obtained image is stored as image data, a large amount of image data can be stored for a long time period without causing deterioration of the image, and developments to a medical diagnostic information system, etc. can be realized.

FIG. 8 shows an example of a radiation image reading apparatus and a radiation image processing apparatus using the photostimulable phosphor sheet. A photostimulable phosphor sheet 31, on which a radiation image is recorded, is set to a predetermined position of the reading apparatus. The photostimulable phosphor sheet 31 is conveyed in Y-direction by a sheet conveying means 33 driven by a motor 32. On the other hand, a light beam (excitation light) 35 generated from a laser light source 34 is reflected and deflected by a rotary polygon mirror 37, which is driven by a motor 36 and rotated at high speed in an arrow direction, and passes through a convergent lens 38. Thereafter, an optical path of the light beam 35 is changed by a mirror 39, and the photostimulable phosphor sheet 31 is scanned by the light beam 35 in X-direction. By the scanning, photostimulated luminescence light 40 is generated from a part of the photostimulable phosphor sheet 31 irradiated by the light beam 35. A light amount of the photostimulated luminescence light 40 corresponds to radiation image information accumulated and recorded on the sheet. The photostimulated luminescence light 40 is guided by an optical guide 41, and is photo-electrically detected by a photomultiplier (multiplier phototube) 42. An analog signal output from the photomultiplier 42 is amplified by an amplifier 43, and is digitized by an A/D converter 44. The digital signal is transmitted as image data to an image processing apparatus 45.

In such a process of reading photostimulated luminescence light, there is also a case where "pre-reading" of the data is executed. The "pre-reading" is executed by scanning the photostimulable phosphor sheet 31 in advance by light beam at a low level to read an image recorded on the sheet schematically so that image data obtained by the pre-reading is analyzed. Thereafter, "main reading" is executed by irradiating a light beam at a level higher than that of the light beam irradiated in the pre-reading and scanning the sheet to read the image data in optimal reading condition according to a dosage of the irradiated radiation, etc.

The image processing apparatus 45 includes an input unit 46 having a keyboard or a mouse for inputting instructions or information, a driving unit 47 for operating a floppy disk, etc. as an auxiliary recording medium, a display 48 such as a CRT for displaying a visible image on the basis of the image data and a main body section 49 having a central processing unit (CPU), an internal memory, an interface for transmitting and receiving signals between the CPU and a hard disk as a recording medium, an image reading apparatus, and so on.

When the image data is received by the image processing apparatus 45, the received image data is analyzed and subjected to image processing such as normalization, gradation processing or logic reading processing. Then, the processed image is displayed on the display 48. Thereafter, processing of outputting the processed image on a film, etc. is executed by using a printer or the like and the output result is supplied for diagnosis.

The visible image obtained by the radiation image reading apparatus using the above-mentioned photostimulable phosphor sheet and the radiation image processing apparatus is normally printed on a film and is used in the medical diagnosis. At this time, various arrangements can be considered, such as an arrangement of recording one picture on one entire film, an arrangement of recording two pictures on one film in parallel with each other leftward and rightward or upward and downward, an arrangement of recording four pictures on one film and so on. In particular, in a case where it is desired to compare left-hand image with right-hand image as in mammography (breasts) or in a case where it is desired to observe front image and side image in parallel with each other as in the entire spine, a plurality of pictures are often displayed on one film, which will be called as a "multi-format output" hereinafter.

However, according to a conventional multi-format output, a plurality of pictures are output in a uniform format irrespective of kinds of the pictures. Therefore, clearances are formed between the plurality of pictures, which makes it difficult to compare the plurality of pictures with each other and to understand relation between the plurality of pictures.

Japanese patent application laid-open JP-A-3-287248 discloses a scoliosis diagnostic system for photo-electrically reading a radiation image of the spine recorded on the photostimulable phosphor sheet having a recording area corresponding to an entire length of the spine as an object to be photographed, executing image processing to reduce the read radiation image and outputting the reduced radiation image.

Further, Japanese patent application laid-open JP-A-8-294479 discloses a computer-supported image diagnostic apparatus. In the apparatus, an entire radiation image of an object is displayed, while local image data representing an image in a local area including a detected abnormal shading candidate is extracted from the entire image data. The image in the local area is displayed separately from the entire image on the basis of the local image data. The above-mentioned JP-A-8-294479 also discloses the following contents. In the case where X-ray images of breasts, etc. are to be displayed, an entire image of one breast and an entire image of the other breast are displayed simultaneously and adjacently back to back, for example. The local area including the abnormal shading candidate detected from the entire image data of the one breast, and a local area with respect to the same portion of the other breast are displayed in window areas arranged on the screen displaying the respective entire images so that corresponding portions of both two breasts can be directly compared and observed.

Further, Japanese patent application laid-open JP-A-9-238933 discloses a breast image display apparatus. In the case where pair images constructed by arranging a pair of left-hand and right-hand breast images back to back are displayed, the breast image display apparatus displays the selected one of a vertical direction pair image obtained by photographing the pair of left-hand and right-hand breasts from a vertical direction, a side direction pair image obtained by photographing the pair of breasts from a side direction, and a pair image with a local enlarged image partially including a local area enlarged image obtained by enlarging the local area including the abnormal shading candidate within the vertical direction pair image and the side direction pair image so as to improve observation and photograph reading performance.

However, at the actual scene of medical diagnosis, images are processed with respect to various objects by using the same apparatus. Therefore, it has been necessary for a user to select a format which conforms to each of the images every time when a portion of an object to be photographed such as the entire spine or the mammography is changed.

SUMMARY OF THE INVENTION

The present invention was accomplished in view of such problems. Accordingly, an object of the present invention is to provide an image processing method and an apparatus having control means able to change an output-format in accordance with the photographing condition.

To solve the above problems, a medical image processing method, according to the present invention, of processing image data representing an image obtained by radiography and read by an image reading apparatus comprises the steps of: receiving the image data and photographing condition when the image is obtained; executing image processing of the image data; reading output-format control information corresponding to the photographing condition from a predetermined set of output-format control information to be used to control an image format when the image is output on a film; and constructing layout of the image to be output on the basis of the read output-format control information.

A medical image processing apparatus, according to the present invention, for processing image data representing an image obtained by radiography and read by an image reading apparatus comprises: means for receiving the image data and photographing condition when the image is obtained; means for executing image processing of the image data; and means for reading output-format control information corresponding to the photographing condition from a predetermined set of output-format control information to be used to control an image format when the image is output on a film.

In the present invention, since the image is constructed in accordance with the output-format which is set on the basis of the photographing condition, each image can be output on films in the optimal format for respective one of medical diagnoses.

BRIEF DESCRIPTION OF THE DRAWINGS

FIGS. 3A to 3D are front views typically showing the position relation of an object, a recording sheet and an irradiating direction of radiation in four directions in photographing mammography, and showing pictures photographed in the respective directions;

FIG. 4 is a view showing photographing condition and output-format control information in photographing mammography;

DESCRIPTION OF THE PREFERRED EMBODIMENTS

Figure 1:
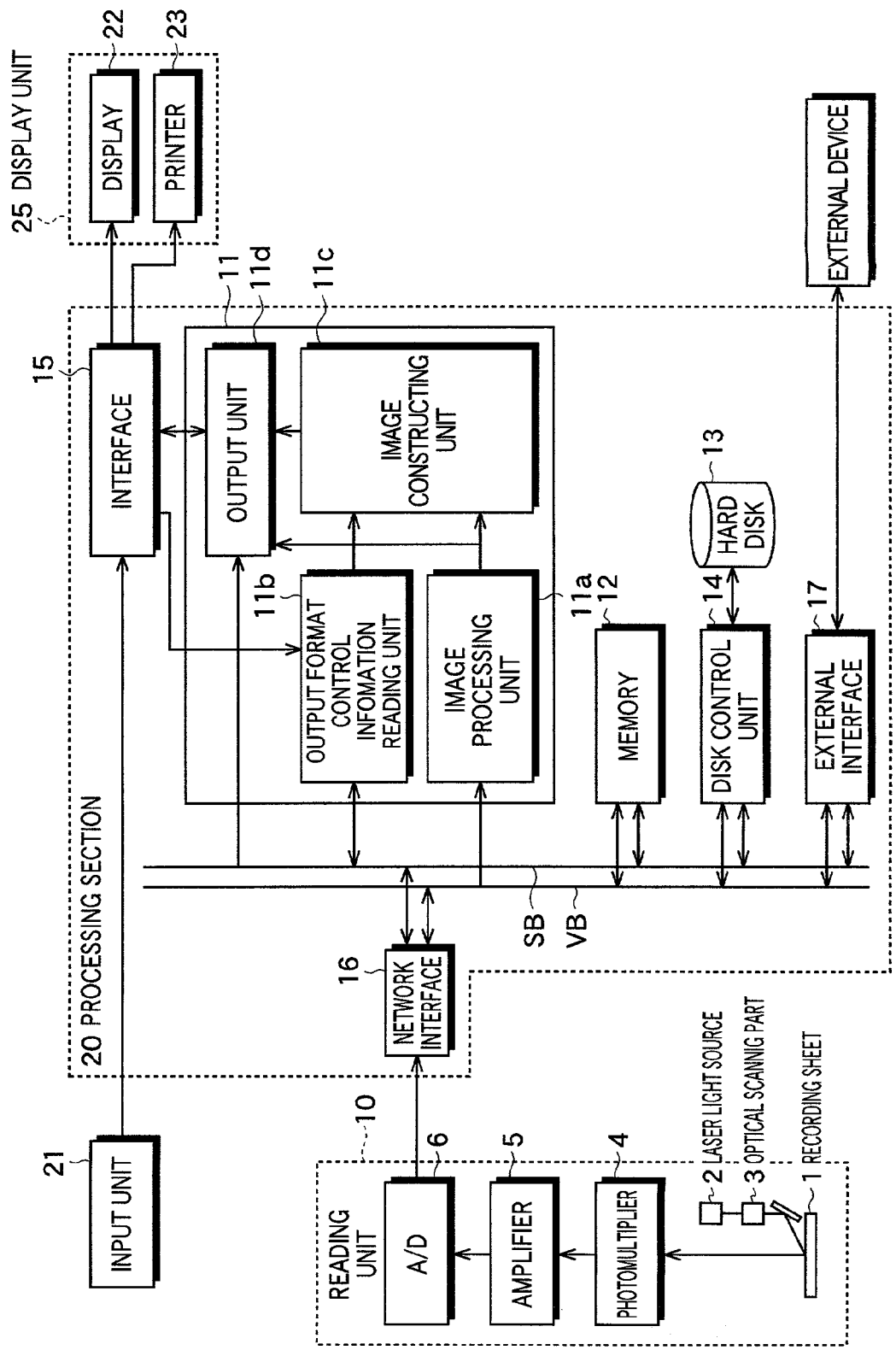
FIG. 1 is a view showing the construction of a system including a medical image processing apparatus according to one embodiment of the present invention.

Embodiments of the present invention will now be described in detail with reference to the drawings. The same constituent elements are designated by the same reference numerals and explanation thereof will be omitted.

FIG. 1 is a view showing construction of a medical image processing system including a medical image processing apparatus according to one embodiment of the present invention. In the embodiment, a recording sheet used in radiography is coated with photostimulable phosphor substance and records information of an object by being irradiated with radiation.

The recording sheet (photostimulable phosphor sheet) 1, on which a radiation image is recorded by the radiography, is set to a predetermined position of a reading unit 10. A light beam generated from a laser light source 2 passes through an optical scanning part 3 to scan a surface of the recording sheet 1. By this scanning, the recording sheet 1 is irradiated with excitation light and an amount of photostimulated luminescence light according to accumulated and recorded radiation image information is generated from the irradiated part. The photostimulated luminescence light is photo-electrically detected by a photomultiplier (multiplier phototube) 4, and is output as an analog signal. The analog signal is amplified by an amplifier 5 and is digitized by an A/D converter 6. The digital signal is transmitted as image data to a processing section 20.

In the processing section 20, a central processing unit (hereinafter called as CPU) 11 is connected to each unit through a system bus SB or a video bus VB. The processing section 20 includes an internal memory 12, a hard disk 13 as a recording medium for recording programs and databases to be used for operation of the CPU 11, and a hard disk control unit 14. Further, an input unit 21 such as a keyboard or a mouse for inputting instructions or information, a display unit 25 including a display 22 such as a CRT for displaying a visible image on the basis of image data and a printer 23 for printing the visible image are connected to the CPU 11 through an interface 15. Further, a floppy disk, an externally attached hard disk, MO, MT, RAM, CD-ROM, DVD-ROM and so on can be also used as a recording medium in addition to the built-in hard disk. It is also considered that an external device connected through a network is used as an output destination of the visible image or the image data. In this case, signals are transmitted and received through an external interface 17 between the external device and the CPU 11.

An operation of the CPU 11 will be explained. Image data output from the reading unit 10 is transmitted to the CPU 11 through a network interface 16. An image processing unit 11a executes image processing such as normalization, gradation processing or logic reading processing. On the other hand, when photographing condition is input from the input unit 21 to the CPU 11 through the interface 15, an output-format control information reading unit 11b reads output-format control information corresponding to the received photographing condition from the hard disk 13. An image constructing unit 11c constructs layout of the image data subjected to the above-mentioned image processing on the basis of the read output-format control information. A constructed picture is output to the display 22 or the printer 23 through the interface 15.

In this embodiment, each of the image processing unit 11a, the output-format control information reading unit 11b, the image constructing unit 11c and the output unit 11d as shown in FIG. 1 is constructed by the CPU which operates on the basis of a program, but can be also constructed by a digital circuit or an analog circuit. Further, the output-format control information may be recorded on a recording medium such as a hard disk, a floppy disk, MO, MT, RAM, CD-ROM, or DVD-ROM.

Figure 2:
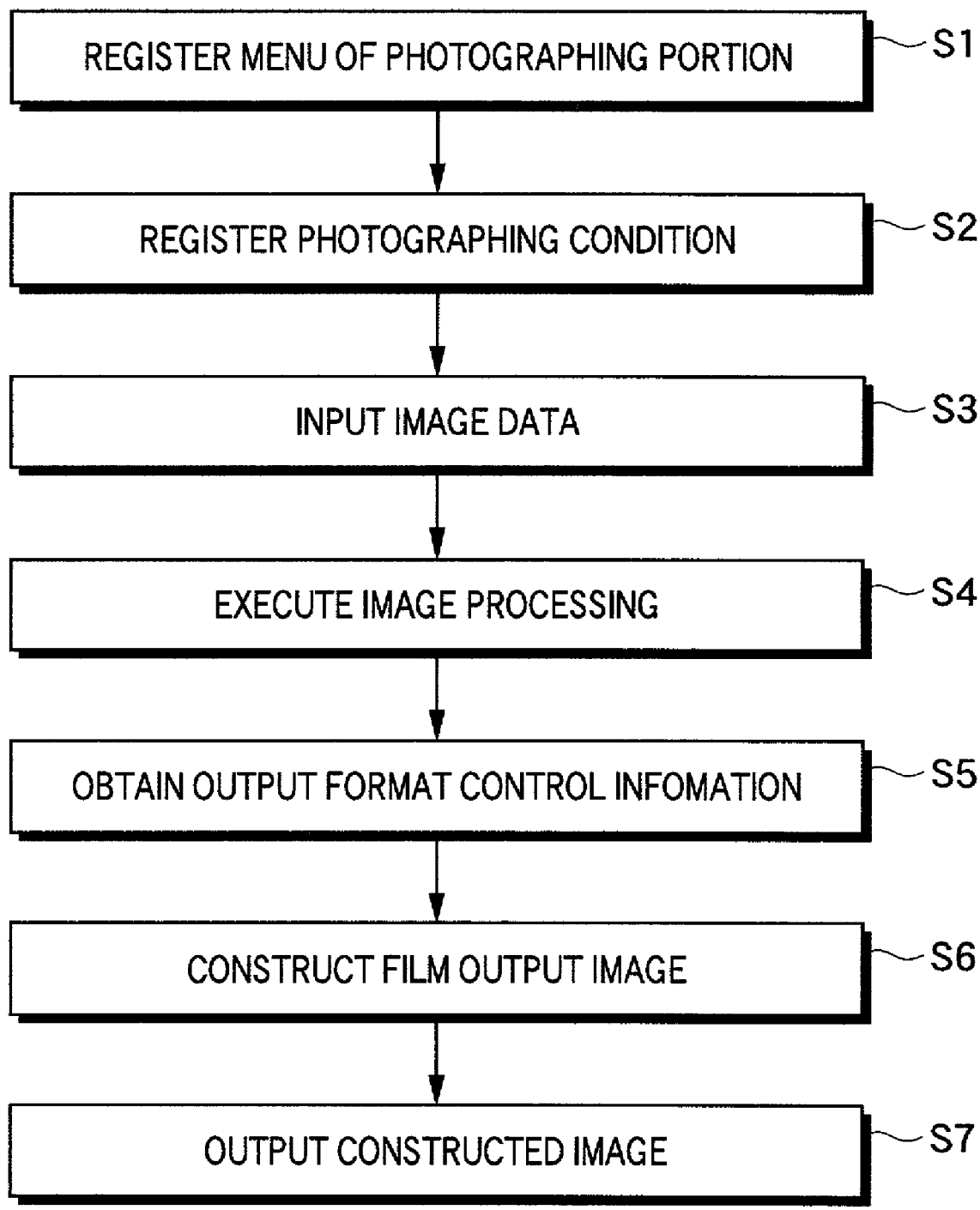
FIG. 2 is a flow chart showing a medical image processing method according to a first embodiment of the present invention.

Next, a medical image processing method according to a first embodiment of the present invention will be explained. FIG. 2 is a flow chart showing the medical image processing method according to the first embodiment of the present invention.

At step S1, a user selects and registers a portion to be photographed, for example, "mammography" or "entire spine" in accordance with a photography menu. A case of the mammography will be explained below.

In the case of photographing the mammography, a total of four photographs are generally taken in which one photograph is taken from an inside slanting upside and the other photograph is taken from just above with respect to each of left-hand and right-hand breasts. FIGS. 3A to 3D typically show relation of an object 100 seen from a front face in photography of the mammography and a recording sheet 30 and an irradiating direction of radiation. In FIG. 3A, the right-hand breast is photographed from the inside slanting upside, and an image as shown by an oblique line portion of a picture 30a is recorded on the recording sheet 30 irradiated by the radiation in an arrow direction. Also, the right-hand breast is photographed from just above in FIG. 3B, the left-hand breast is photographed from just above in FIG. 3C, and the left-hand breast is photographed from the inside slanting upside in FIG. 3D. Images of the object 100 as shown by oblique line portions of respective pictures 30b to 30d in FIGS. 3B to 3D are recorded on the recording sheets 30 irradiated by the radiation in respective directions.

When the menu of the mammography is registered, four kinds of photographing condition as shown in FIGS. 3A to 3D are registered at step S2. As to the photographing condition, there are detailed contents of portions to be photographed, irradiating directions of the radiation (photographing directions) and so on as shown in FIG. 4.

At step S3, an image data and photographing condition under which the image is obtained are input. At step S4, image processing such as normalization, gradation processing or logic reading processing is executed for the image data on the basis of respective image processing condition set in accordance with the photographing condition.

At step S5, output-format control information is obtained on the basis of the registered photographing condition for each image data set. As the output-format control information, "inversion", "output position", "output size" and so on can be also included in addition to "rotation" or "position adjustment" as shown in FIG. 4. Further, the output-format control information may also include such information as "two-picture construction with no clearance between first and second pictures". Such output-format control information is stored in advance in a database in correspondence with the photographing condition. Further, one kind of the output-format control information or a combination of plural kinds of the output-format control information is set for each photographing condition.

Figure 5A:
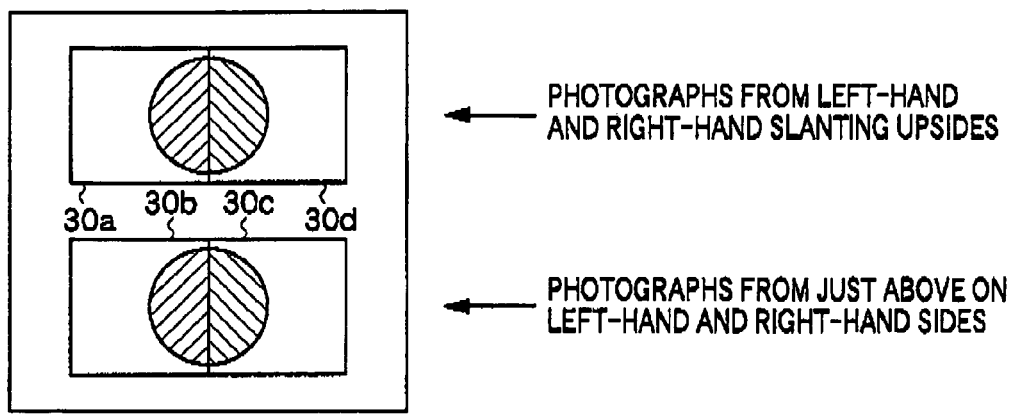
FIG. 5A is a view showing an image constructed on the basis of output-format control information.
Figure 5B:
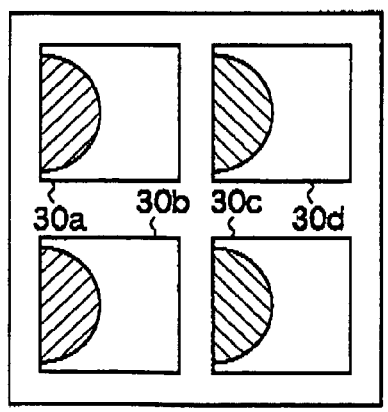
FIG. 5B is a view showing an image constructed in an original output-format as it is.

At step S6, an output image of each image data set is constructed on the basis of the obtained output-format control information. Referring to FIGS. 3A to 3D again, such processing as "determination of the output position of an image", "rotation" or "position adjustment" is executed with respect to the image data set constituting the pictures 30a to 30d, on the basis of the output-format control information corresponding to the photographing condition as shown in FIG. 4. Then, the output image as shown in FIG. 5A is constructed. For comparison, an image constructed in an original output-format is shown in FIG. 5B.

At this time, the user may make a preview of the above-mentioned output image to be displayed on the display. Also, the user may adjust the picture while seeing the preview picture. Thereafter, at step S7, the constructed image is output on a film, etc. by a printer and a desirable visible image is obtained.

Thus, according to this embodiment, each image can be output on the film in an optimal output-format set for that image in accordance with the photographing condition.

Figure 6:
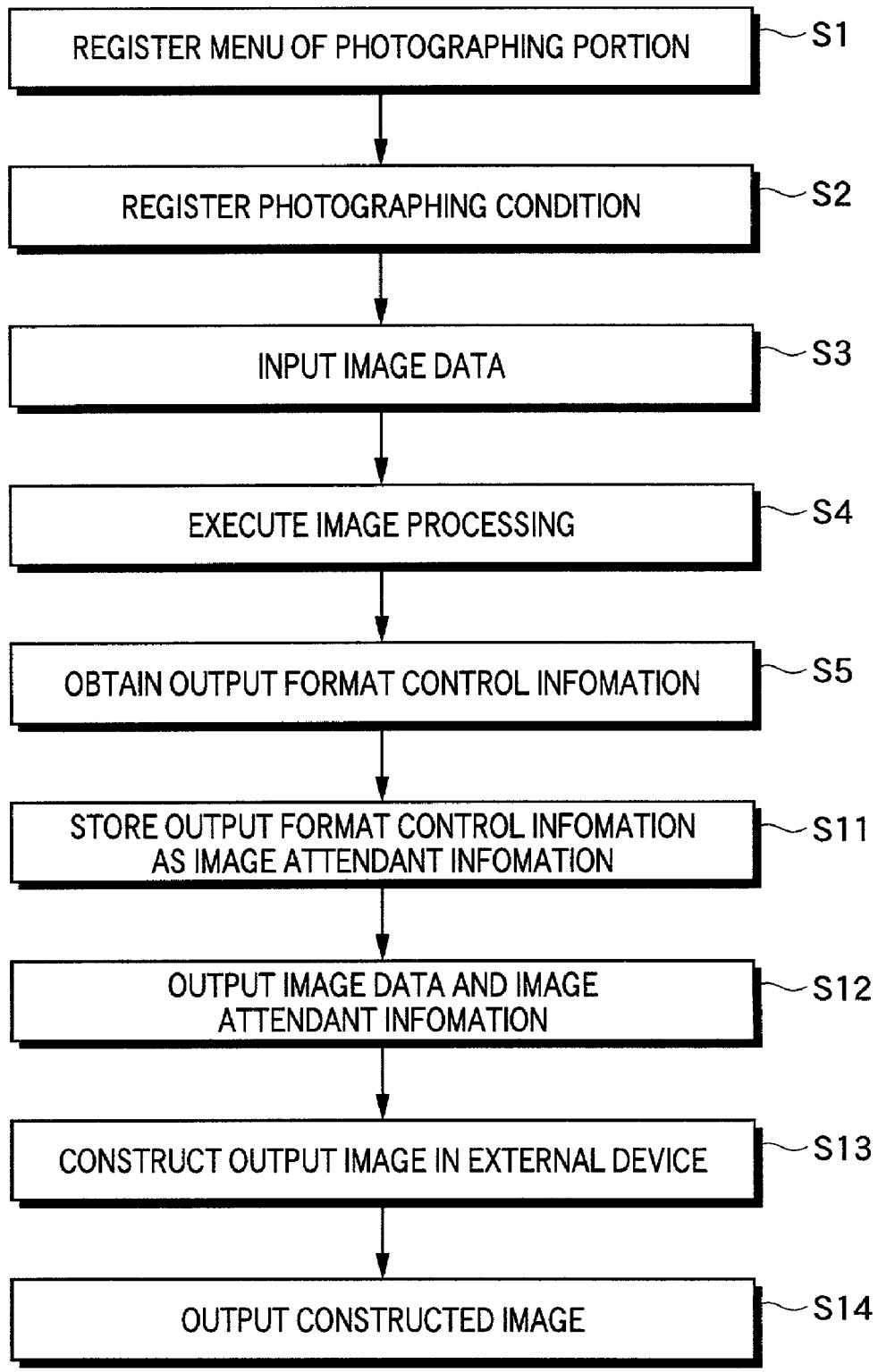
FIG. 6 is a flow chart showing a medical image processing method according to a second embodiment of the present invention.

A medical image processing method according to a second embodiment of the present invention will next be explained. FIG. 6 is a flow chart showing the medical image processing method according to the second embodiment of the present invention. This embodiment can be applied in a case where an external device for outputting the visible image has a function of constructing the output image on the basis of image attendant information.

Similar to the medical image processing method according to the first embodiment of the present invention, when the user registers the photography menu at step S1, one or plural kind of photographing condition is registered in accordance with a portion to be photographed registered in the menu at step S2. At step S3, image data and the photographing condition under which the image is obtained are input. At step S4, image processing is executed with respect to the image data on the basis of image processing condition set in accordance with the photographing condition. At step S5, output-format control information is obtained for each image data set on the basis of the photographing condition.

At step S11, the obtained output-format control information is stored as attendant information of the image together with other attendant information (for example, a name of a patient, a photographing place, etc.). At step S12, the processed image data and the image attendant information are output to the external device connected through the external interface 17 (see FIG. 1). At step S13, the external device, which has received the data, constructs an output image of a visible image on the basis of the image attendant information. Subsequently, at step S14, the constructed image is output on a film, etc., then the user can obtain a desirable visible image.

According to this embodiment, since the image data and the image attendant information are output as data itself, the data can be communized between a plurality, if exist, of devices which are able to construct the image on the basis of the image attendant information. Accordingly, development to a medical diagnosis information processing system connected by a network can be attained.

Figure 7:
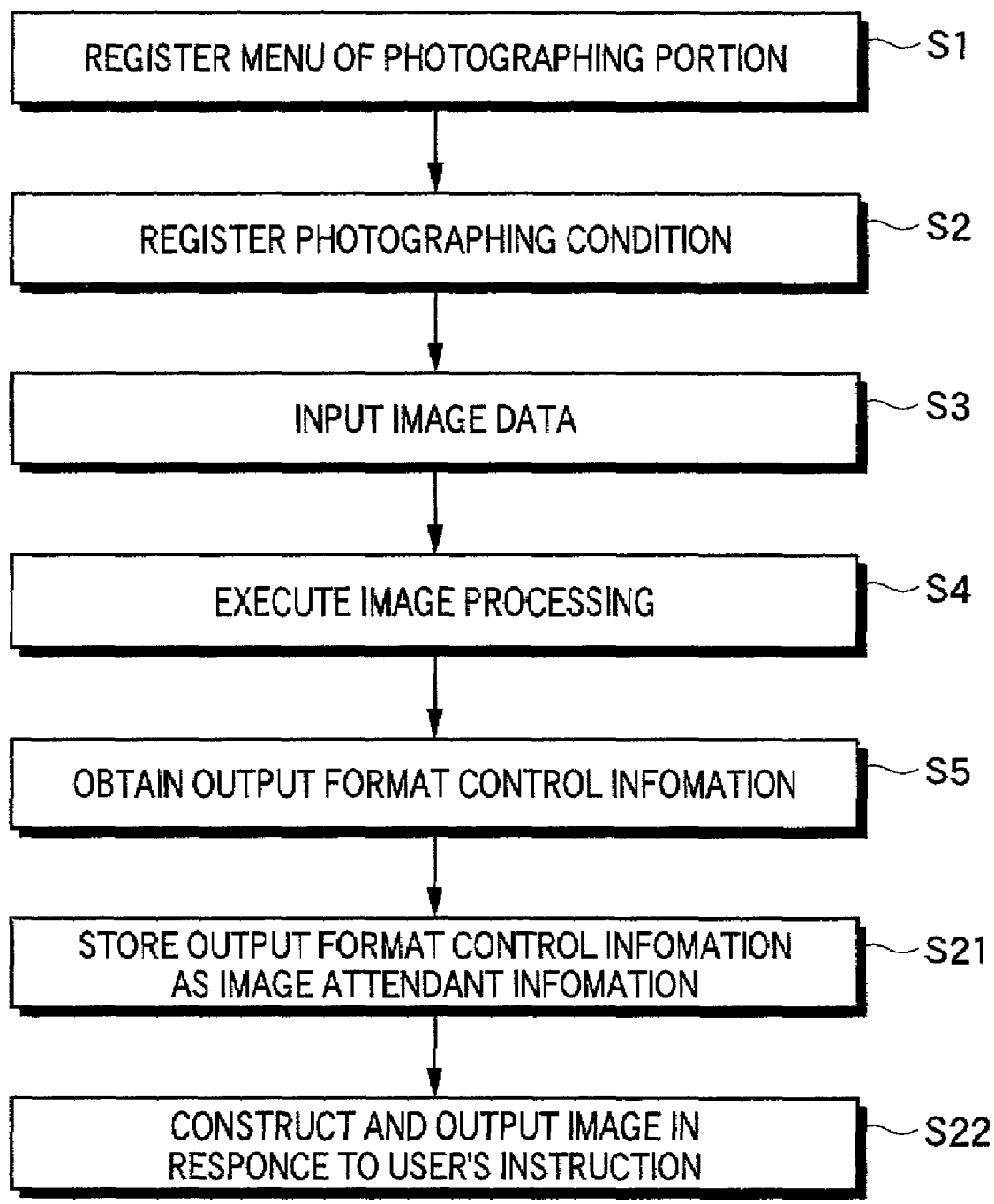
FIG. 7 is a flow chart showing a medical image processing method according to a third embodiment of the present invention.
Figure 8:
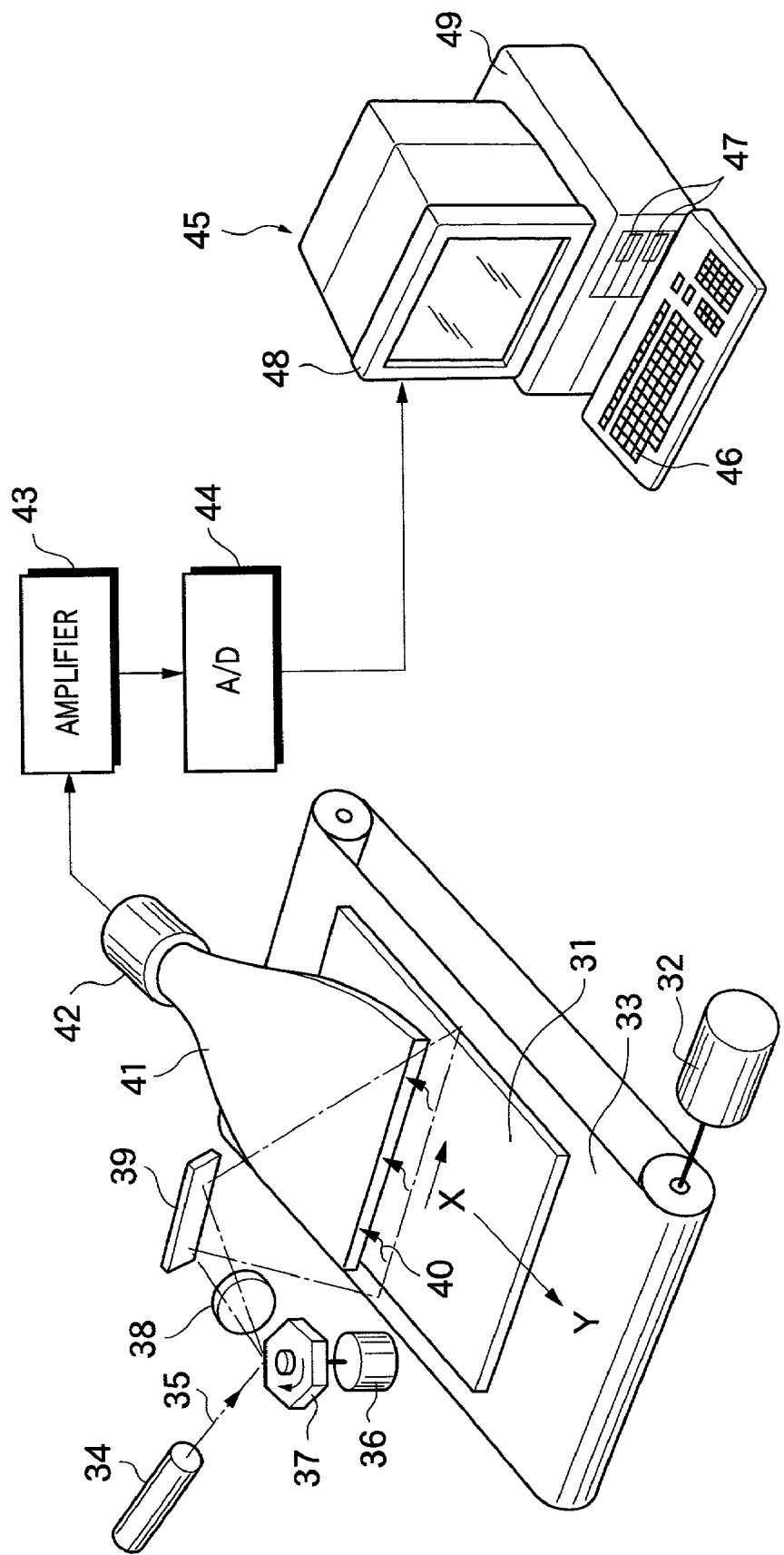
FIG. 8 is a view showing construction of a system including a conventional medical image processing apparatus.

Next, a medical image processing method according to a third embodiment of the present invention will be explained. FIG. 7 is a flow chart showing the medical image processing method according to the third embodiment of the present invention. In this embodiment, the output-format control information is stored together with the image data so that each user can select a desirable format as to whether the image is output which has been constructed on the basis of the output-format control information or the image is output in the original format.

Similar to the medical image processing method according to the first embodiment of the present invention, when the user registers the photography menu at step Si, one or plural kind of photographing condition is registered in accordance with a portion to be photographed registered in the menu at step S2. At step S3, image data and photographing condition under which the image is obtained are input. At step S4, image processing is executed with respect to the image data on the basis of image processing condition set in accordance with the photographing condition. At step S5, output-format control information is obtained on the basis of the photographing condition for each image data set.

At step S21, the obtained output-format control information is stored as image attendant information together with the image data set. When a visible image is output, a user can give instruction as to whether the visible image is output which has been constructed on the basis of the image attendant information as shown in FIG. 5A or the visible image is output in the original output-format as shown in FIG. 5B. Further, at this time, the user can also adjust the picture while seeing a preview picture. Thereafter, at step S22, the user can obtain a desirable visible image by instructing to output the visible image.

According to this embodiment, since the output image is constructed by the user's instruction, each user can obtain the desirable visible image even when there are a plurality of plural users.

As mentioned above, according to the present invention, it becomes possible to provide visible images output in respective optimal formats for respective medical diagnoses by obtaining information from among a predetermined information set for controlling an output-format on the basis of the photographing condition and constructing the visible images. Further, a medical image processing apparatus can be provided which outputs such visible images.

The invention claimed is:

1. A medical image processing method of processing image data representing a series of images obtained by a radiography apparatus and read by an image reading apparatus, said method comprising the steps of:
   (a) receiving the plural kinds of image data representing the series of images and respective photographing conditions when the series of images are obtained;
   (b) executing image processing of the plural kinds of image data;
   (c) automatically obtaining output-format control information including information as to output position, rotation and position adjustment of the series of images corresponding to the photographing conditions received at step (a) from among a predetermined set of output-format control information to be used to control an image format when the series of images are to be output in one screen; and
   (d) automatically constructing a layout of the series of images to be output in one screen on the basis of the output-format control information obtained at step (c).

2. A medical image processing method according to claim 1, wherein each of said photographing conditions is determined in accordance with a portion to be photographed.

3. A medical image processing method according to claim 1, further comprising the steps of:
   storing the obtained output-format control information as image attendant information of the image data; and
   outputting one of (i) the image series of images after the image processing and (ii) the series of images in the layout constructed on the basis of the stored output-format control information, in accordance with a user's instruction.

4. A medical image processing method according to claim 1, further comprising a the step of:
   previewing and adjusting the series of images to be output in one screen.

5. A medical image processing method according to claim 1, wherein said output-format control information includes information to be used to control at least one of an output position, a position adjustment, an output size, a rotating state and an inverting state of the image.

6. A medical image processing apparatus for processing image data representing a series of images obtained by a radiography apparatus and read by an image reading apparatus, said apparatus comprising:

first means for receiving the plural kinds of image data representing the series of images and respective photographing conditions when the series of images are obtained;

second means for executing image processing of the plural kinds of image data;

third means for automatically obtaining output-format control information including information as to output position, rotation and position adjustment of the series of images corresponding to the photographing conditions received by said first means from among a predetermined set of output-format control information to be used to control an image format when the series of images are to be output in one screen; and fourth means for automatically constructing a layout of the series of images to be output in one screen on the basis of the output-format control information obtained by said third means.

7. A medical image processing apparatus according to claim 6, further comprising:

means for storing the read obtained output-format control information as image attendant information of the image data; and means for outputting one of (i) the series of images after the image processing and (ii) the series of images in the layout constructed on the basis of the stored output-format control information, in accordance with a user's instruction.

8. A medical image processing apparatus for processing image data representing a series of images obtained by a radiography apparatus and read by an image reading apparatus, said apparatus comprising:

first means for receiving plural kinds of image data representing the series of images and respective photographing conditions when the series of images are obtained;

second means for executing image processing of the plural kinds of image data;

third means for automatically obtaining output-format control information including information as to output position, rotation and position adjustment of the series of images corresponding to the photographing conditions received by said first means from among a predetermined set of output-format control information to be used to control an image format when the series of images are to be output in one screen;

fourth means for storing the obtained output-format control information as image attendant information of the image data; and fifth means for outputting the image data and the image attendant information.

9. A medical image processing apparatus according to claim 6, wherein each of said photographing conditions is determined in accordance with a portion to be photographed.

10. A medical image processing apparatus according to claim 8, wherein each of said photographing conditions is determined in accordance with a portion to be photographed.

11. A medical image processing apparatus according to claim 6, further comprising:

means for previewing and adjusting the series of images to be output in one screen.

12. A medical image processing apparatus according to claim 8, further comprising:

means for previewing and adjusting the series of images to be output in one screen on the film.

13. A medical image processing apparatus according to claim 6, wherein said output-format control information includes information to be used to control at least one of an output position, a position adjustment, an output size, a rotating state and an inverting state of the image.

14. A medical image processing apparatus according to claim 8, wherein said output-format control information includes information to be used to control at least one of an output position, a position adjustment, an output size, a rotating state and an inverting state of the image.

15. A medical image processing apparatus according to claim 8, further comprising:

means for automatically constructing a layout of a series of images to be output in one screen on the basis of input image data and image attendant information; and means for outputting the image constructed in the constructed layout.

* * * * *